United States Patent
Badylak et al.

(10) Patent No.: US 10,736,991 B2
(45) Date of Patent: Aug. 11, 2020

(54) NON-GELLING SOLUBLE EXTRACELLULAR MATRIX WITH BIOLOGICAL ACTIVITY

(71) Applicants: University of Pittsburgh—Of the Commonwealth System of Higher Education, Pittsburgh, PA (US); The University of Nottingham, Nottingham (GB)

(72) Inventors: Stephen F. Badylak, West Lafayette, IN (US); Timothy Joseph Keane, Jr., Wellsboro, PA (US); Lisa Jane White, Nottingham (GB)

(73) Assignees: University of Pittsburgh—Of the Commonwealth System of Higher Education, Pittsburgh, PA (US); The University of Nottingham (GB)

( * ) Notice: Subject to any disclaimer, the term of this patent is extended or adjusted under 35 U.S.C. 154(b) by 0 days.

(21) Appl. No.: 15/760,864

(22) PCT Filed: Sep. 16, 2016

(86) PCT No.: PCT/US2016/052261
§ 371 (c)(1),
(2) Date: Mar. 16, 2018

(87) PCT Pub. No.: WO2017/049167
PCT Pub. Date: Mar. 23, 2017

(65) Prior Publication Data
US 2019/0060521 A1    Feb. 28, 2019

Related U.S. Application Data

(60) Provisional application No. 62/220,409, filed on Sep. 18, 2015.

(51) Int. Cl.
| | | |
|---|---|---|
| A61L 27/36 | (2006.01) | |
| A61L 27/54 | (2006.01) | |
| A61L 27/02 | (2006.01) | |
| A61L 27/10 | (2006.01) | |
| A61L 27/12 | (2006.01) | |
| A61L 27/06 | (2006.01) | |
| A61L 27/34 | (2006.01) | |

(52) U.S. Cl.
CPC ......... *A61L 27/3687* (2013.01); *A61L 27/025* (2013.01); *A61L 27/06* (2013.01); *A61L 27/10* (2013.01); *A61L 27/12* (2013.01); *A61L 27/34* (2013.01); *A61L 27/3633* (2013.01); *A61L 27/54* (2013.01); *A61L 2300/414* (2013.01); *A61L 2300/426* (2013.01); *A61L 2300/606* (2013.01); *A61L 2300/64* (2013.01); *A61L 2400/18* (2013.01); *A61L 2420/02* (2013.01)

(58) Field of Classification Search
CPC .. A61L 27/3633; A61L 27/3687; A61L 27/06; A61L 27/34; A61L 27/025; A61L 27/12; A61L 27/10
See application file for complete search history.

(56) References Cited

U.S. PATENT DOCUMENTS

| | | |
|---|---|---|
| 4,902,508 A | 2/1990 | Badylak et al. |
| 4,956,178 A | 9/1990 | Badylak et al. |
| 5,281,422 A | 1/1994 | Badylak et al. |
| 5,352,463 A | 10/1994 | Badylak et al. |
| 5,372,821 A | 12/1994 | Badylak et al. |
| 5,554,389 A | 9/1996 | Badylak et al. |
| 5,573,784 A | 11/1996 | Badylak et al. |
| 5,645,860 A | 7/1997 | Knapp, Jr. et al. |
| 5,711,969 A | 1/1998 | Patel et al. |
| 5,753,267 A | 5/1998 | Badylak et al. |
| 5,762,966 A | 6/1998 | Knapp, Jr. et al. |
| 5,866,414 A | 2/1999 | Badylak et al. |
| 6,099,567 A | 8/2000 | Badylak et al. |
| 6,485,723 B1 | 11/2002 | Badylak et al. |
| 6,576,265 B1 | 6/2003 | Spievack |
| 6,579,538 B1 | 6/2003 | Spievack |
| 6,696,270 B2 | 2/2004 | Badylak et al. |
| 6,783,776 B2 | 8/2004 | Spievack |
| 6,793,939 B2 | 9/2004 | Badylak |
| 6,849,273 B2 | 2/2005 | Spievack |

(Continued)

FOREIGN PATENT DOCUMENTS

| | | |
|---|---|---|
| WO | 2011087743 A2 | 7/2011 |
| WO | 2013009595 A2 | 1/2013 |

OTHER PUBLICATIONS

Ringel et al., "The Application of Tissue Engineering Procedures to Repair the Larynx", Journal of Speech, Language, and Hearing Research, 2006, pp. 194-208, vol. 49.

(Continued)

*Primary Examiner* — Mina Haghighatian
(74) *Attorney, Agent, or Firm* — TheWebb Law Firm (57) ABSTRACT

Provided are methods for preparing non-gelling, solubilized extracellular matrix (ECM) materials useful as cell growth substrates. Also provided are compositions prepared according to the methods as well as uses for the compositions. In one embodiment a device, such as a prosthesis, is provided which comprises an inorganic matrix into which the non-gelling, solubilized ECM composition is dispersed to facilitate in-growth of cells into the ECM and thus adaptation and/or attachment of the device to a patient. In another embodiment, the composition is delivered intraarticularly, intrathecally, intraoccularly, intracranially, and into pleural space.

20 Claims, 5 Drawing Sheets

(56) References Cited

U.S. PATENT DOCUMENTS

| | | | |
|---|---|---|---|
| 6,852,339 B2 | 2/2005 | Spievack | |
| 6,861,074 B2 | 3/2005 | Spievack | |
| 6,887,495 B2 | 5/2005 | Spievack | |
| 6,890,562 B2 | 5/2005 | Spievack | |
| 6,890,563 B2 | 5/2005 | Spievack | |
| 6,890,564 B2 | 5/2005 | Spievack | |
| 6,893,666 B2 | 5/2005 | Spievack | |
| 8,361,503 B2 | 1/2013 | Badylak et al. | |
| 8,691,276 B2 | 4/2014 | Badylak et al. | |
| 8,741,352 B2 | 6/2014 | Hodde et al. | |
| 10,004,827 B2* | 6/2018 | Badylak | A61K 35/12 |
| 10,213,526 B2* | 2/2019 | Badylak | A61L 27/52 |
| 2010/0196480 A1 | 8/2010 | Hiles et al. | |
| 2010/0226895 A1 | 9/2010 | Boruch | |
| 2011/0224484 A1* | 9/2011 | Case | A61F 2/2475 |
| | | | 600/37 |
| 2014/0356331 A1* | 12/2014 | Badylak | A61L 27/3633 |
| | | | 424/93.7 |

OTHER PUBLICATIONS

Sarikaya et al., "Antimicrobial Activity Associated with Extracellular Matrices", Tissue Engineering, 2002, pp. 63-71, vol. 8, No. 1.
Sawkins et al., "Hydrogels derived from demineralized and decellularized bone extracellular matrix", Acta Biomateriala, 2013, pp. 7865-7873, vol. 9.
White et al., "Effective terminal sterilization using supercritical carbon dioxide", Journal of Biotechnology, 2006, pp. 504-515, vol. 123, No. 4.

\* cited by examiner

| lyophilized | 0.01N HCl reconstituted | ddH$_2$O reconstituted | EtO sterilized: reconstituted in water |

Fig. 4A     Fig. 4B     Fig. 4C     Fig. 4D

Non-sterilized      EtO Sterilized ddH₂O reconstituted
SIS-ECM pre-gel

Fig. 5

EtO Sterilized ddH₂O reconstituted
UBM pre-gel

NON-GELLING SOLUBLE EXTRACELLULAR MATRIX WITH BIOLOGICAL ACTIVITY

CROSS REFERENCE TO RELATED APPLICATIONS

This application is the United States national phase of International Application No. PCT/US2016/052261 filed Sep. 16, 2016, and claims the benefit of U.S. Provisional Patent Application No. 62/220,409 filed Sep. 18, 2015, the disclosures of which are hereby incorporated in their entirety by reference.

BACKGROUND

Methods of preparation of extracellular matrix-(ECM-) derived gels are described herein.

The use of extracellular matrix (ECM) scaffolds is commonplace as these scaffolds have been shown to accommodate tissue remodeling in numerous tissues. Soluble forms of ECM, which form a hydrogel at body temperature (37° C.), are increasingly used in anatomic locations that do not permit the use of an ECM scaffold. Similar to ECM scaffolds, the ECM hydrogels have biological effects that include immune modulation and recruitment of stem cells, among others. However, all therapeutic applications do not require a hydrogel and a non-gelling soluble form of ECM may be preferred in many instances, e.g., intra-articular injections, enema solutions, etc.

SUMMARY

Described herein is the preparation and biologic effects of a non-gelling soluble form of ECM. A solubilized ECM product, especially one that has not been dialyzed and/or crosslinked, has the ability to form a hydrogel when pH- and salt balanced, and warmed to 37° C. Many therapeutic applications do not require or may preclude the use of a hydrogel. In such cases, a non-gelling soluble ECM may be preferred.

Solubilization of ECM can be achieved by enzymatic digestion (e.g., pepsin). To ensure that the mixture is non-gelling, ECM is sterilized (e.g., by exposure to ethylene oxide, gamma-irradiation, or electron beam irradiation), e.g., in solid sheet form or in comminuted powder form. The soluble form of ECM following these processing steps does not form a hydrogel—a typical feature of solubilized ECM—but retains the biological effects that have implications in a wide range of potential therapeutics. Results of in-vitro studies show that the non-gelling soluble ECM promotes the migration/chemotaxis of a multipotent stem cell, and stimulates macrophages in the same manner as an ECM hydrogel.

The technology will be useful in applications where inflammation reductions and/or tissue repair is necessary, but restrictions in anatomy would preclude the use of a material that will swell and/or take up considerable space. For example, injections could be delivered intraarticularly, intrathecally, intraoccularly, intracranially, or into pleural space.

DETAILED DESCRIPTION

The use of numerical values in the various ranges specified in this application, unless expressly indicated otherwise, are stated as approximations as though the minimum and maximum values within the stated ranges are both preceded by the word "about". In this manner, slight variations above and below the stated ranges can be used to achieve substantially the same results as values within the ranges. Also, unless indicated otherwise, the disclosure of ranges is intended as a continuous range including every value between the minimum and maximum values. As used herein "a" and "an" refer to one or more.

As used herein, the term "comprising" is open-ended and may be synonymous with "including", "containing", or "characterized by". The term "consisting essentially of" limits the scope of a claim to the specified materials or steps and those that do not materially affect the basic and novel characteristic(s) of the claimed invention. The term "consisting of" excludes any element, step, or ingredient not specified in the claim. As used herein, embodiments "comprising" one or more stated elements or steps also include, but are not limited to embodiments "consisting essentially of" and "consisting of" these stated elements or steps.

Methods are described herein of preparing extracellular matrix (ECM)-derived compositions comprising solubilized extracellular matrix obtained from any of a variety of tissues. Related compositions, devices and methods of use also are described. The compositions are non-gelling when their temperature is raised to 37° C. According to one non-limiting embodiment, the ECM-derived composition is an injectable solution at 37° C. According to certain aspects, the composition is bioactive because the entire, intact ECM is solubilized and is not dialyzed, cross-linked and/or otherwise treated to remove or otherwise inactivate ECM structural or functional components, resulting in a highly bioactive composition. A general set of principles for preparing a non-gelling, solubilized ECM-derived composition is provided, along with specific protocols for preparing such compositions. In comparison, non-limiting examples of gelling (reverse-gelling) ECM-derived compositions are described in U.S. Pat. No. 8,361,503, and United States Patent Publication Nos. 2010-0226895, and International Patent Publication Nos. WO 2011/087743 and WO 2013/009595.

As used herein, "sterilized", "terminal sterilization", or "terminally sterilized" refers to the complete, essentially complete, or practically complete sterilization of a composition or device. This does not include disinfection, e.g., with peracetic acid during preparation of an ECM material as part of or ancillary to decellularization. As an example of disinfection, an ECM material can be disinfected by immersion in 0.1% (v/v) peracetic acid (a), 4% (v/v) ethanol, and 96% (v/v) sterile water for 2 h. The ECM material is then washed twice for 15 min with PBS (pH=7.4) and twice for 15 min with deionized water. Although this is characterized as disinfection, it is typically not acceptable under current regulatory practice as a terminal sterilization method. During terminal sterilization, products are exposed to a validated process that kills living microorganisms. In the context of ECM products, decellularized ECM material can be exposed to terminal sterilization before solubilization, storage and/or commercial distribution. A variety of methods for terminal sterilization are known in the art, including exposure to: ethylene oxide, propylene oxide, gamma radiation, electron beam radiation, gas plasma sterilization, and supercritical carbon dioxide (see, e.g., White, A, et al., "Effective Terminal Sterilization Using Supercritical Carbon Dioxide," (2006) *J. Biotech.* 123(4):504-515).

The composition may also be disinfected by treatment with glutaraldehyde, which causes cross linking of the protein material, but this treatment substantially alters the material such that it is slowly resorbed or not resorbed at all and incites a different type of host remodeling which more closely resembles scar tissue formation or encapsulation rather than constructive remodeling. Cross-linking of the protein material can also be induced with carbodiimide or dehydrothermal or photooxidation methods. Cross-linked ECM material is not considered to be a useful ECM material for purposes herein.

As indicated in the Examples below, the timing of terminal sterilization substantially affects the ability of a digested, solubilized ECM material to form a hydrogel by reverse gelling. Sterilization is performed on a wet or dry solid sheet form or in comminuted powder form prior to enzymatic digestion with, e.g., an acid protease. By "dry" or "dried" it is meant dried or lyophilized to a point that essentially all water is removed from a composition, recognizing that in practice, one may not literally remove all water molecules from any composition. Thus "dry" or "dried" refers to a water content of, for example and without limitation, less than 5.0, 1.0, 0.5, 0.1, 0.01, 0.001 or 0.0001% by weight of the composition (% wt.). Material can be dried by any process, such as, for example and without limitation, by simple evaporation at any non-damaging temperature, such as at room temperature, or by lyophilization (freeze drying).

According to one aspect of the invention, a method of preparing a non-gelling, solubilized ECM material is provided. In the method, decellularized or devitalized tissue, that is, extracellular matrix (ECM) material is terminally sterilized, for example by electron beam or gamma radiation, exposure to ethylene oxide gas or to supercritical carbon dioxide. It is then solubilized by digestion with an acid protease, such as trypsin or pepsin, in an acidic solution to produce a digest solution. The digest solution optionally can be dried or is dried, for example by air drying or lyophilization. The composition can be stored, packaged and/or distributed in this dried, e.g., lyophilized, state. The sterilized material is then hydrated, for instance by solubilization in water or in an aqueous solution such as a TRIS buffer or PBS, or a salt solution such as a sodium chloride solution, such as (0.9%) saline to produce a sterilized digest solution. The sterilized digest solution is then brought to a pH between 7.2 and 7.8, e.g., 7.4, to produce a neutralized digest solution, for example, by mixing the solution with an isotonic buffer or a base, such as, without limitation NaOH. The solution does not gel at 37° C., allowing the composition to remain as a solution at physiological temperatures. The rehydration and neutralization may be combined by rehydrating the dried, sterilized composition in a buffer, such as PBS at pH 7.2-7.8, which will accomplish the rehydration and neutralization step concurrently.

The compositions described herein find use as, without limitation, an injectable graft (e.g., xenogeneic, allogeneic or autologous) for tissues, for example, bone or soft tissues, in need of repair or augmentation most typically to correct trauma or disease-induced tissue defects. Virtually any administration route is contemplated, including topical, enteral, and parenteral routes. The compositions also may be used as a lavage for rinsing external or internal, e.g., lumenal, surfaces, for therapeutic effect. For example, the composition may be used on the skin or on an external wound. The composition also can be administered orally, nasally, by inhalation, enterally, intravaginally, etc. For example, injections could be delivered intraarticularly, intrathecally, intraoccularly, intracranially, and into pleural space.

The compositions may be implanted into a patient, human or animal, by a number of methods. In one non-limiting embodiment, the compositions are injected as a liquid into a desired site in the patient. As used herein, the term "seed," "seeding," or "seeded" refers to the addition, incorporation, propagation of, or spreading of a defined volume of a cell suspension or a defined cell number into a specific composition. The composition may be pre-seeded with cells, and then preferably injected using a larger-bore, e.g. 16 gauge needle, to prevent shearing of cells.

As used herein, the terms "extracellular matrix" and "ECM" refer to a natural scaffolding for cell growth that is prepared by decellularization of tissue found in multicellular organisms, such as mammals and humans. ECM can be further processed by, for instance dialysis or cross-linking. ECM is a complex mixture of structural and non-structural biomolecules, including, but not limited to, collagens, elastins, laminins, glycosaminoglycans, proteoglycans, antimicrobials, chemoattractants, cytokines, and/or growth factors. In mammals, ECM often comprises about 90% collagen, in its various forms. The composition and structure of ECMs vary depending on the source of the tissue. For example, small intestine submucosa (SIS), urinary bladder matrix (UBM) and liver stroma ECM each differ in their overall structure and composition due to the unique cellular niche needed for each tissue.

As used herein, the terms "intact extracellular matrix" and "intact ECM" refers to an extracellular matrix that retains activity of its structural and non-structural biomolecules, including, but not limited to, collagens, elastins, laminins, glycosaminoglycans, proteoglycans, antimicrobials, chemoattractants, cytokines, and/or growth factors, such as, without limitation comminuted ECM as described herein. The activity of the biomolecules within ECM can be removed chemically or mechanically, for example, by cross-linking and/or by dialyzing the ECM. ECM material useful for preparation of the non-gelling ECM material described herein essentially has not been cross-linked and/or dialyzed, meaning that the ECM has not been subjected to a dialysis and/or a cross-linking process. Thus, ECM that is cross-linked and/or dialyzed (in anything but a trivial manner which does not substantially affect the functional characteristics of the ECM in its uses described herein) is not considered to be useful for the methods or compositions described herein.

By "biocompatible", it is meant that a device, scaffold composition, etc. is essentially, practically (for its intended use) and/or substantially non-toxic, non-injurious or non-inhibiting or non-inhibitory to cells, tissues, organs, and/or organ systems that would come into contact with the device, scaffold, composition, etc.

An "ECM material," is a material comprising or that is prepared from an extracellular matrix-containing tissue, and does not consist of a single, isolated and purified ECM component, such as a purified collagen preparation, as are commercially available. Any type of tissue-derived material can be used to produce the ECM materials in the methods, compositions and devices as described herein (see generally, U.S. Pat. Nos. 4,902,508; 4,956,178; 5,281,422; 5,352,463; 5,372,821; 5,554,389; 5,573,784; 5,645,860; 5,771,969; 5,753,267; 5,762,966; 5,866,414; 6,099,567; 6,485,723; 6,576,265; 6,579,538; 6,696,270; 6,783,776; 6,793,939; 6,849,273; 6,852,339; 6,861,074; 6,887,495; 6,890,562; 6,890,563; 6,890,564; and 6,893,666). In certain embodiments, the ECM material is isolated from a vertebrate animal, for example and without limitation, from a mammal, including, but not limited to, human, monkey, pig, cow and sheep. The ECM material can be prepared from any organ or tissue, including without limitation, urinary bladder, intestine, liver, esophagus and dermis.

In one embodiment, the ECM is isolated from a urinary bladder. In another embodiment, the ECM is isolated from intestine, or a portion thereof. The intestine extends from the pyloric sphincter to the anus, and includes: the small intestine, extending from the pyloric valve to the ileocecal valve; the large intestine, extending from the ileocecal valve; and portions thereof, including: the duodenum; the jejunum; the ileum; the cecum; the appendix; the ascending, transverse, descending and sigmoid colon; the rectum and/or the anal canal. The ECM may or may not include the basement membrane portion of the ECM. In certain embodiments, the ECM includes at least a portion of the basement membrane.

The type of ECM used in the scaffold can vary depending on the intended cell types to be recruited during wound healing or tissue regeneration, the native tissue architecture of the tissue organ to be replaced, the availability of the tissue source of ECM, or other factors that affect the quality of the final scaffold and the possibility of manufacturing the scaffold. For example and without limitation, the ECM may contain both a basement membrane surface and a non-basement membrane surface, which would be useful for promoting the reconstruction of tissue such as the urinary bladder, esophagus, or blood vessel all of which have a basement membrane and non-basement membrane component.

In general, a method of preparing an ECM material as described herein requires the preparation of ECM material from an animal of a specific species, and typically from a specific organ. In certain aspects, the ECM material is prepared from mammalian tissue. As used herein, the term "mammalian tissue" refers to tissue obtained from a mammal, wherein tissue comprises any cellular component of an animal. For example and without limitation, tissue can be obtained from aggregates of cells, an organ, portions of an organ, or combinations of organs. In certain aspects, the ECM material is prepared from tissue of a vertebrate animal, for example and without limitation, human, monkey, pig, cattle, and sheep. In certain aspects, the ECM material is prepared from any tissue of an animal, for example and without limitation, urinary bladder, liver, CNS, adipose tissue, small intestine, large intestine, colon, esophagus, pancreas, dermis, and heart. In one aspect, the ECM material is prepared from urinary bladder tissue, optionally excluding the basement membrane portion of the tissue.

Following isolation of the tissue of interest, decellularization (devitalization) is performed by various methods, for example and without limitation, exposure to hypertonic saline, peracetic acid, Triton-X or other detergents. Decellularized tissue (ECM material) can then be dried, either lyophilized (freeze-dried) or air dried. Dried ECM material can be comminuted by methods including, but not limited to, tearing, milling, cutting, grinding, and shearing. The comminuted ECM material can also be further processed into a powdered form by methods, for example and without limitation, such as grinding or milling in a frozen or freeze-dried state.

As used herein, the term "comminute" and any other word forms or cognates thereof, such as, without limitation, "comminution" and "comminuting", refers to the process of reducing larger particles into smaller particles, including, without limitation, by grinding, blending, shredding, slicing, milling, cutting, shredding. ECM can be comminuted while in any form, including, but not limited to, hydrated forms, frozen, air-dried, lyophilized, powdered, sheet-form.

As described above, the ECM material is terminally sterilized, and solubilized. In order to prepare solubilized ECM material, comminuted ECM material is digested with an acid protease in an acidic solution to form a digest solution. As used herein, the term "acid protease" refers to an enzyme that cleaves peptide bonds, wherein the enzyme has increased activity of cleaving peptide bonds in an acidic pH. For example and without limitation, acid proteases can include pepsin and trypsin.

The digest solution of ECM material typically is kept at a constant stir for a certain amount of time at room temperature. The ECM digest can be used immediately or be stored at −20° C. or frozen at, for example and without limitation, −20° C. or −80° C., and in the context of the methods and compositions described herein, dried and sterilized. Next, the pH of the digest solution is raised to a pH between 7.2 and 7.8 to produce a neutralized digest solution. The pH can be raised by adding one or more of a base or an isotonic buffered solution, for example and without limitation, NaOH or PBS at pH 7.4. The method typically does not include a dialysis step, yielding a more-complete ECM-like composition. The composition retains more of the qualities of native ECM due to retention of many native soluble factors, such as, without limitation, cytokines.

As used herein, the term "isotonic buffered solution" refers to an isotonic solution that is buffered to a pH between 7.2 and 7.8 and that has a balanced concentration of salts to promote an isotonic environment. As used herein, the term "base" refers to any compound or a solution of a compound with a pH greater than 7. For example and without limitation, the base is an alkaline hydroxide or an aqueous solution of an alkaline hydroxide. In certain embodiments, the base is NaOH or NaOH in PBS.

This neutralized digest solution can, at that point be incubated at a suitably warm temperature, for example and without limitation, at about 37° C. The neutralized digest solution can be frozen and stored at, for example and without limitation, −20° C. or −80° C. As used herein, the term "neutralized digest solution" or "neutralized digest" refers to a digest or digest solution wherein the pH is increased, and can be in the form of a solution or dried composition. For example and without limitation, a neutralized digest has a pH between 7.2 and 7.8.

In one aspect, an active agent or cells can be added to the solubilized ECM material as described herein. For example, cytokine, chemoattractant or cells can be mixed into the composition prior to use. For example and without limitation, useful active agents include growth factors, interferons, interleukins, chemokines, monokines, hormones, angiogenic factors, drugs and antibiotics. Cells mixed into the solubilized ECM material can be autologous or allogeneic with respect to the patient to receive the composition/device comprising the composition. The cells can be stem cells or other progenitor cells, or differentiated cells. In one example, a layer of dermis obtained from the patient is seeded for use in repairing damaged skin and/or underlying tissue. As used herein, the term "active agent" refers to any compounds or compositions having a preventative or therapeutic effect, including and without limitation, antibiotics, peptides, hormones, organic molecules, vitamins, supplements, factors, proteins and chemoattractants.

As used herein, the terms "cell" and "cells" refer to any types of cells from any animal, such as, without limitation, rat, mice, monkey, and human. For example and without limitation, cells can be progenitor cells, such as stem cells, or differentiated cells, such as endothelial cells, smooth muscle cells. In certain embodiments, cells for medical procedures can be obtained from the patient for autologous procedures or from other donors for allogeneic procedures.

The composition described herein can be used in multi-layered tissue constructs, for example electrosprayed, e.g., onto or concurrently with an electrodeposited synthetic polymer composition, such as an elastomer.

In another embodiment of the pre-molded composition, the ECM composition is contained within or absorbed into or adsorbed onto a laminar sheath of non-comminuted and non-digested ECM tissue, such as SIS or UBM, to add physical strength to the composition. In this embodiment, sheets of ECM tissue, prepared in any manner known in the art, can be placed into a mold prior, and the non-gelling composition is added to the mold. The sheets of ECM tissue may be used as the mold, so long as they are formed and sewn or cross-linked into a desired shape. In this manner, a solid composition can be produced that has greater physical strength than is the case of the composition described herein.

In another aspect, the solubilized ECM material is injected into a patient. The composition is injected at a locus in the patient where the matrix is needed for cell growth. For example and without limitation, where a patient has had tissue removed due to trauma, debridement and/or removal of damaged, diseased or cancerous tissue, the composition can be injected at the site of tissue removal to facilitate in-growth of tissue. The viscosity of the composition can be controlled by varying the amounts of water (e.g., by varying the amounts of water, acid, base, buffer (such as PBS) or other diluents) used to prepare the composition. In applications in which a small gauge needle is used, such as in endoscopy, a less viscous composition would be needed. In applications in which a larger gauge needle is available, a more viscous composition can be used. Also, use of a larger gauge needle, irrespective of the viscosity of the composition, favors mixing of live cells with the composition immediately prior to implantation with less risk of shearing the cells.

In yet another aspect, the solubilized ECM material is contained in a spray device, for spraying onto tissue, a wound, etc.

In one aspect, the ECM material is directly injected into a patient. In one embodiment, the composition is in a frozen state and is thawed and warmed prior to injection.

In a further embodiment, a commercial kit is provided comprising a composition described herein. A kit comprises suitable packaging material and the composition. In one non-limiting embodiment, the kit comprises a solubilized ECM material in a vessel, which may be the packaging, or which may be contained within packaging. The composition may be frozen, cooled; e.g., kept at near-freezing temperatures, such as, without limitation, below about 4° C. or kept at room temperature, e.g., 20-25° C., or even at physiological temperatures, for instance in preparation for use. In another non-limiting embodiment, the kit comprises a first vessel containing dried, e.g. lyophilized, non-gelling, solubilized ECM material as described herein. The vessel may be a vial, syringe, tube or any other container suitable for storage and transfer in commercial distribution routes of the kit.

As used herein, the term "hybrid inorganic/ECM scaffold" refers to an ECM material that is coated onto a biocompatible inorganic structure, such as, without limitation, a metal, an inorganic calcium compound such as calcium hydroxide, calcium phosphate or calcium carbonate, or a ceramic composition. In one embodiment, ultrasonication is used to aid in coating of the inorganic structure with the ECM-derived composition. As used herein, the term "ultrasonication" refers to the process of exposing ultrasonic waves with a frequency higher than 15 kHz and lower than 400 kHz.

As used herein, the term "coat", and related cognates such as "coated" and "coating," refers to a process comprising of covering an inorganic structure with the solubilized ECM material. For example and without limitation, coating of an inorganic structure with a solubilized ECM material as described herein includes methods such as pouring, embedding, layering, dipping, spraying.

In another aspect, the solubilized ECM material is coated onto a biocompatible structural material, such as a metal, an inorganic calcium compound such as calcium hydroxide, calcium phosphate or calcium carbonate, or a ceramic composition. Non-limiting examples of suitable metals are cobalt-chrome alloys, stainless steel alloys, titanium alloys, tantalum alloys, titanium-tantalum alloys, which can include both non-metallic and metallic components, such as molybdenum, tantalum, niobium, zirconium, iron, manganese, chromium, cobalt, nickel aluminum and lanthanum, including without limitation, CP Ti (commercially pure titanium) of various grades or Ti 6Al4V (90% wt. Ti, 6% wt. Al and 4% wt. V), stainless steel 316, Nitinol (Nickel-titanium alloy), titanium alloys coated with hydroxyapatite. Metals are useful due to high strength, flexibility, and biocompatibility. Metals also can be formed into complex shapes and many can withstand corrosion in the biological environments, reduce wear, and not cause damage to tissues. In one non-limiting example, the metal is femoral or acetabular component used for hip repair. In another example, the metal is a fiber or other protuberance used in permanent attachment of a prosthesis to a patient. Other compositions, including ceramics, calcium compounds, such as, without limitation, aragonite, may be preferred, for example and without limitation, in repair of or re-shaping of skeletal or dental structures. Combinations of metal, ceramics and/or other materials also may prove useful. For instance, a metal femoral component of a hip replacement may comprise a ceramic ball and/or may comprise a plastic coating on the ball surface, as might an acetabular component.

Metals, as well as other materials, as is appropriate, can be useful in its different forms, including but not limited to wires, foils, beads, rods and powders, including nanocrystalline powder. The composition and surface of metals or other materials can also be altered to ensure biocompatibility, such as surface passivation through silane treatments, coating with biocompatible plastics or ceramics, composite metal/ceramic materials. The materials and methods for their employment are well-known in the field of the present invention.

A difficulty with using metal inserts to repair a patient's skeletal structure is that the inserts must be anchored/attached to existing skeletal parts. Traditional methods employ cement and/or screws. In the case of prostheses, the prostheses are not connected to a patient's tissue except, typically, by cementing. Therefore, it is desirable to biologically attach a patient's tissue to a medical device. This may be accomplished by coating surfaces of the implant with the solubilized ECM material described herein, which will facilitate in-growth of tissue and thus attachment of the device. A variety of porous structures can be attached to the implant to create a scaffold into which the solubilized ECM material, and later cells or other tissue (e.g., bone) can infiltrate. Structures include, without limitation: woven or non-woven mesh, sponge-like porous materials, fused beads, etc. The porous scaffold will facilitate formation of a strong bond between living tissue, including bone, and the device. The "pores" of the porous scaffold may be of any size that will permit infiltration of a solubilized ECM material, optionally facilitated by ultrasound or other treatments that would assist in permeation of the composition, and later cells or other biological materials, such as bone, cartilage, tendons, ligaments, fascia or other connective tissue, into the scaffolding. In one aspect, metal fibers are attached to the device, and the metal fibers are coated with a solubilized ECM material described herein, thereby permitting in-growth of tissue within the fibers. In a second embodiment, a matrix of small beads is welded or otherwise attached to a surface of the device and a solubilized ECM material described herein is coated onto the bead matrix, facilitating in-growth of tissue among the beads. In one example, a device contains a protuberance of fibers, which can be inserted inside a bone, permitting fusion of the metal fibers with the bone. In one aspect, the solubilized ECM material is seeded and incubated with a suitable cell population, such as autologous osteoblasts, to facilitate bone in-growth.

A device (e.g., a prosthesis) as described herein can be coated with the described ECM composition. In another embodiment, the composition is applied to the device or prostheses. The composition on the device can then be dried, e.g. lyophilized and the entire device can be terminally sterilized, followed by packaging and distribution. The lyophilized product on the device can be hydrated by an end-user.

In use, the device which is coated with a suitable scaffolding and ECM composition as described herein may be contacted with cells, e.g. of a patient or allogeneic cells, and the cells are allowed to infiltrate the matrix. The in-growth or infiltration of cells can occur in vivo or ex vivo, depending on optimization of methods. For example and without limitation, in the case of a femoral implant, the implant can be inserted into the femur and cells of a patient, and desirable bone tissue, infiltrates the scaffolding to fuse the device to the bone. In another embodiment, for example in the case of an artificial tendon or ligament, a biopsy of a patient's tendons or ligaments is incubated with an appropriate scaffold in order to create an autologous ligament or tendon graft.

EXAMPLES

Example 1—Preparation of Porcine Extracellular Matrix (ECM) (UBM)

Figure 1:
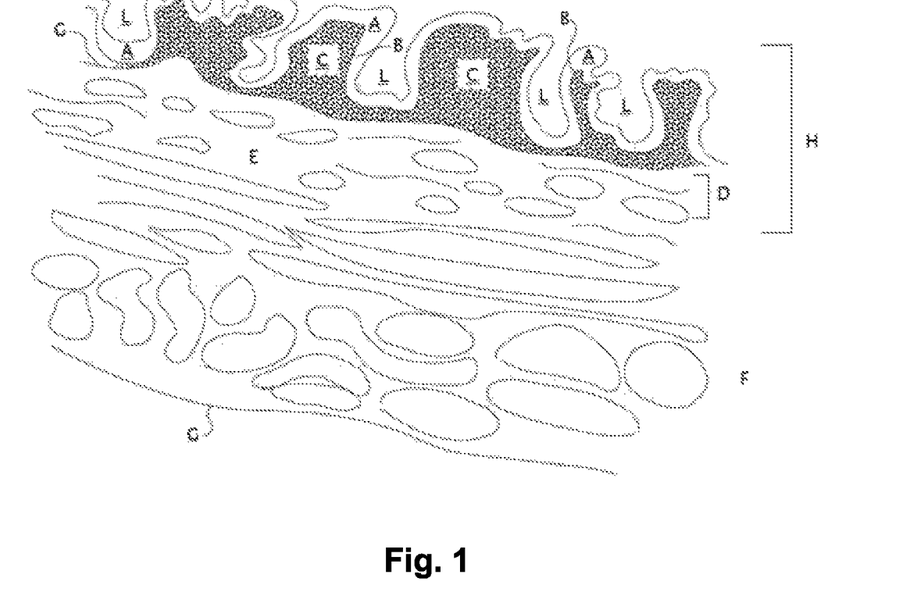
FIG. 1 is a schematic of a cross-sectional view of the wall of the urinary bladder (not drawn to scale). The following structures are shown: epithelial cell layer (A), basement membrane (B), tunica propria (C), muscularis mucosa (D), tunica submucosa (E), tunica muscularis externa (F), tunica serosa (G), tunica mucosa (H), and the lumen of the bladder (L).

The preparation of UBM has been previously described (Sarikaya A, et al. Tissue Eng. 2002 Feb.; 8(1):63-71; Ringel R L, et al. J Speech Lang Hear Res. 2006 Feb.; 49(1):194-208). In brief, porcine urinary bladders were harvested from 6-month-old 108-118 kg pigs (Whiteshire-Hamroc, Ind.) immediately following euthanasia. Connective tissue and adipose tissue were removed from the serosal surface and any residual urine was removed by repeated washes with tap water. The tunica serosa, tunica muscularis externa, the tunica submucosa, and majority of the tunica muscularis mucosa were mechanically removed. The urothelial cells of the tunica mucosa were dissociated from the luminal surface by soaking the tissue in 1.0 N saline solution yielding a biomaterial composed of the basement membrane plus the subjacent tunica propria, which is referred to as urinary bladder matrix (UBM). See FIG. 1 for cross-sectional view of the wall of the urinary bladder, as well as structures included within.

Figure 2A:
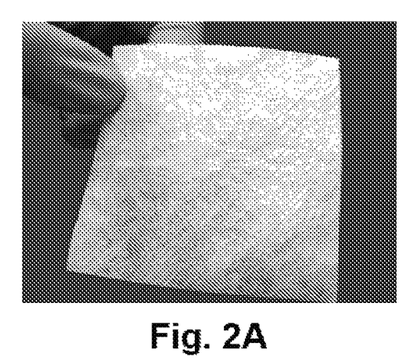
FIG. 2A is a photograph of lyophilized porcine urinary bladder matrix (UBM) sheet.
Figure 2B:
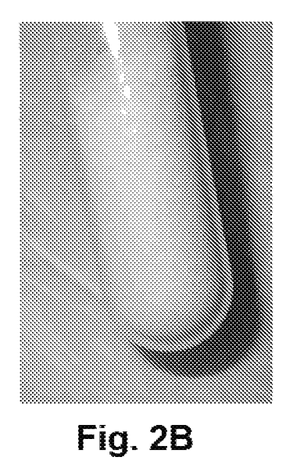
FIG. 2B is a photograph of lyophilized porcine urinary bladder matrix (UBM) powder.

The UBM sheets were disinfected for two hours on a shaker in a solution containing 0.1% (v/v) peracetic acid, 4% (v/v) ethanol, and 95.9% (v/v) sterile water. The UBM sheets (as in FIG. 2A) were then lyophilized (FIG. 2B) using a FTS Systems Bulk Freeze Dryer Model 8-54 and powdered using a Wiley Mini Mill.

Example 2—Preparation of Porcine Spleen ECM

Fresh spleen tissue was obtained. Outer layers of the spleen membrane were removed by slicing, where remaining tissue was cut into uniform pieces. Remnants of outer membrane were trimmed, then rinsed three times in water. Water was strained by using a sieve. Splenocytes were lysed by massaging. Spleen slices were incubated in a solution of 0.02% trypsin/0.05% EDTA at 37° C. for 1 hour in a water bath. If necessary, splenocytes were further lysed by massaging. After rinsing, slices were soaked in 3% Triton X-100 solution and put on a shaker for 1 hour. If necessary, splenocytes were further lysed by massaging. Slices were then soaked in 4% deoxycholic acid solution and put on a shaker for 1 hour. After thoroughly rinsing, the purified spleen ECM was stored for further processing. This tissue was disinfected and dried.

Example 3—Preparation of Porcine Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

Example 4—Preparation of Human Liver Stroma ECM

Fresh liver tissue was obtained. Excess fat and tissue were trimmed. Outer layers of the liver membrane were removed by slicing, where remaining tissue was cut into uniform pieces. Remnants of outer membrane were trimmed using a scalpel or razor blade, then rinsed three times in water. Water was strained by using a sieve. Cells were lysed by massaging. Liver slices were incubated in a solution of 0.02% trypsin/0.05% EDTA at 37° C. for 1 hour in a water bath. If necessary, cells were further lysed by massaging. After rinsing, slices were soaked in 3% Triton X-100 solution and put on a shaker for 1 hour. If necessary, cells were further lysed by massaging. Slices were then soaked in 4% deoxycholic acid solution and put on a shaker for 1 hour. After thoroughly rinsing, the purified liver stroma was stored in deionized water for further processing. This tissue was next disinfected with peracetic acid treatment and dried.

Example 5—Preparation of Porcine Ovarian ECM

Fresh ovarian tissue is obtained within 6 hours of harvest. Ovaries were removed and stored in physiological saline tissue until ready for dissection and residual uterine tissue was removed. Longitudinal incisions were made through the hilum of the ovary and the follicles were disrupted. Once all the follicles have been disrupted, the ECM has been harvested from the ovaries. Rinse three times in filtered water and strain the water using a sieve. Cells were lysed by gentle massaging. ECM was incubated in a solution of 0.02% trypsin/0.05% EDTA at 37° C. for 1 hour in a water bath and then rinsed. If necessary, cells were further lysed by massaging. ECM was soaked in 3% Triton X-100 solution and put on a shaker for 1 hour. After rinsing, cells were further lysed by massaging if necessary. Slices were then soaked in 4% deoxycholic acid solution and put on a shaker for 1 hour. After thoroughly rinsing to remove residual surfactant, the ECM was stored in sterile/filtered water until further use. This tissue was next disinfected with peracetic acid treatment and dried.

Example 6—Preparation of Spinal Cord and Dura Mater ECM

Using forceps, scissors and a scalpel, dura mater was removed from porcine spinal cord. The inner dura mater surface was scrapped with scalpel blade to remove any debris. The spinal cord and dura were placed in separate containers and treated in the same manner as below. The spinal cord was cut either longitudinally or in cross-section to increase surface area and placed in a cassette. Optionally tissue was enzymatically treated using trypsin-EDTA for 30 minutes at 37° C. The tissue was incubated in Triton X-100™ (4-octylphenol polyethoxylate) solutions at 3% for periods up to 2-3 days at 4° C. This step was repeated with a solution of Triton X-100™ at 6% and again with a solution of Triton X-100™ at 9%. The spinal cord tissue was incubated in lecithin or lecithin-deoxycholate to remove lipids overnight at 4° C. Dura mater was not subjected to this procedure. Tissue was then washed in Triton X-100™ 3% or SDS 1% for 1-2 hours. The tissue was rinsed in PBS 3X for 15 minutes at room temperature. Then the tissue was incubated in a solution of DNase I for 1 hour at room temperature. The tissue was washed in PBS three times for 15 minutes at room temperature. Lastly, the tissue was washed in deionized water three times for 15 minutes at room temperature. The procedure produced a gel-like acellular spinal cord material, and a sheet of acellular dura mater material.

Example 7—Preparation of Adipose ECM

Frozen adipose tissue was thawed in water and manually massaged to hasten the lysis of cells. Tissue was placed into a flask containing 0.02% trypsin/0.05% EDTA solution and incubated at 37° C. for one hour then rinsed briefly in distilled deionized water (ddH$_2$O) and manually massaged again. Tissue was then placed into a flask containing 3% Triton X-100 and placed on an orbital shaker for 1 hour at room temperature. Following a brief water rinse, tissue was placed into a 4% deoxycholic acid solution and again placed on an orbital shaker for 1 hour at room temperature. Tissue was rinsed three times in water and stored at 4° C. overnight. The tissue was then subjected to a 4% ethanol and 0.1% peracetic acid solution on an orbital shaker for 2 hours at followed by two phosphate buffered saline (PBS, pH 7.4) and two water washes of 15 minutes each at room temperature. The resulting material was then washed in 100% n-propanol for one hour on an orbital shaker at room temperature and washed in four changes of ddH$_2$O for one hour to remove the n-propanol prior to lyophilization.

Example 8—Preparation of Neural-Derived ECM Gel

Murine spinal cord tissue was stored at −80° C. until needed for ECM derivation processing. The material was thawed and the dura mater was removed from the spinal cord, and the spinal cord was then cut into quarters longitudinally of about 1 inch length and uniform thickness. The spinal cord pieces were placed into water overnight at 4° C. and 120 rpm to mechanically-disrupt the native tissue architecture prior to decellularization. After about 18 h the spinal cord pieces were removed from the water by straining onto a mesh or sieve with hole size of about 840 μm. The pieces of spinal cord were collected with forceps and placed into a flask for protease digestion with 0.02% trypsin/0.05% EDTA solution. The digestion was allowed to proceed in a water bath for 1 h at 37° C. while shaking at 120 rpm. After one hour, the solution was strained off and spinal cord tissue was rinsed gently under a stream of water, detangling as required. The spinal cord pieces were returned to the flask, collecting as many smaller tissue pieces as possible from the strainer using forceps. 3% Triton X-100 solution was then added to the flask to begin decellularization of the tissue, which was placed on a shaker for 1 h at 200 rpm. After one hour the tissue was strained, rinsed, and collected. The tissue pieces were placed back into the flask, and then were subjected to osmotic shock for additional decellularization. Hypertonic 1 M sucrose was added to the flask and placed on a shaker for 15 min at 200 rpm. The tissue was strained, rinsed, collected and combined with hypotonic solution (deionized water) and placed on shaker for 15 min at 200 rpm, to lyse any remaining cells. The decellularized tissue was again strained, rinsed, and reclaimed into a flask. 4% deoxycholate solution was added to the flask and placed upon a shaker for 1 h at 200 rpm. Subsequently, the tissue pieces were strained and rinsed repeatedly in type I (ultra-pure) water until all traces of surfactants (bubbles) were removed. The remaining tissue, now enriched into ECM, was collected and disinfected using a peracetic acid solution (made up of Type I water (96%) and 100% EtOH alcohol (4%)) at a ratio of 20:1 peracetic acid solution to weight of ECM, and shaken at 200 rpm for two hours. Following a series of rinse steps in Phosphate Buffered Saline (PBS), the ECM was frozen at −20° C. and then lyophilized until all water was removed.

Example 9—Sterilization of Pre-Digest ECM Materials

Figure 3:
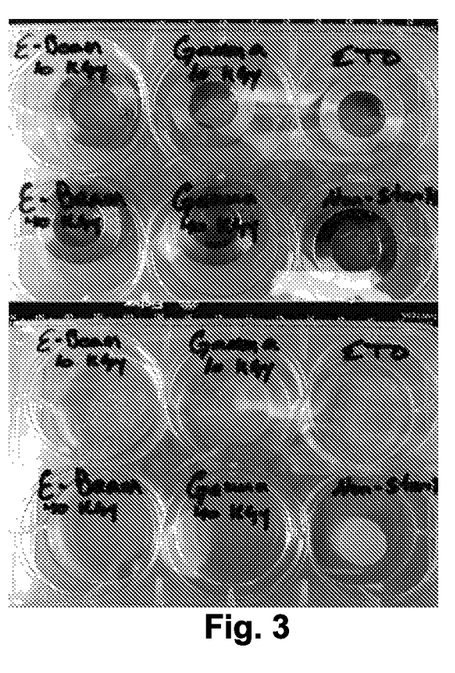
FIG. 3 shows a qualitative observation of hydrogel formation following terminal sterilization. Compared to the non-sterilized controls, the ability of dermal ECM to form a hydrogel following terminal sterilization was abolished after the metallic ring molds (top image) were removed.

It has been noted that terminal sterilization of an ECM scaffold inhibits subsequent hydrogel formation of protease-solubilized ECM materials. The following illustrates the effect of sterilization on qualitative hydrogel formation, using dermal ECM that has not been dialyzed (that is, intact ECM as described above). Porcine dermis was decellularized essentially as described above, and subjected to various methods of terminal sterilization. The dermal ECM sheets were terminally sterilized by exposure to (1) gamma radiation at a dosage of 10 kGy, 25 kGy, and 40 kGy, (2) electron beam radiation at a dosage of 10 kGy, 25 kGy, and 40 kGy, and (3) ethylene oxide (EtO) gas at a dose of 750 mg/h for 16 h. Control dermal ECM sheets were not sterilized. The sterilized and control dermal ECM was then mechanically comminuted in a Wiley Mill with a 60 mesh sieve, enzymatically digested for 48 hours at 4° C. in 1 mg/ml pepsin in a solution of 0.01 N HCl to produce a pre-gel, and tested for hydrogel formation by neutralization to approximately pH 7.4 at room temperature (20-25° C.) and then raising the temperature to 37° C. in an incubator without $CO_2$. FIG. 3 shows the terminally sterilized dermal ECM were unable to form a hydrogel regardless of sterilization method whereas the non-sterilized dermal ECM formed a solid gel and maintained form after removal of metallic ring molds.

Example 10—Sterilization of Lyophilized Product

Figure 4A:
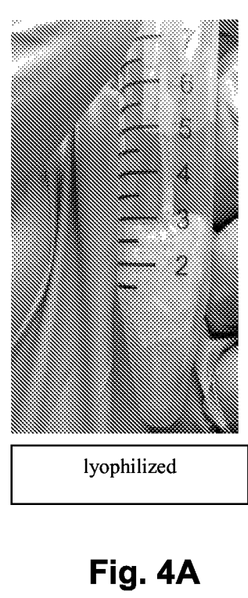
FIG. 4A shows non-sterilized lyophilized pre-gel.
Figure 4B:
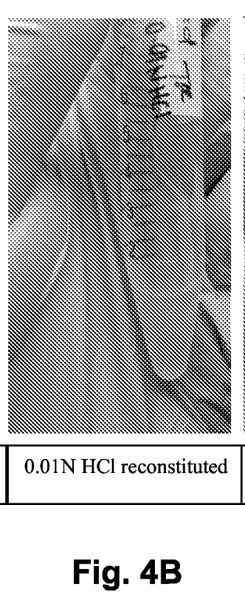
FIG. 4B shows non-sterilized lyophilized pre-gel reconstituted in HCl
Figure 4C:
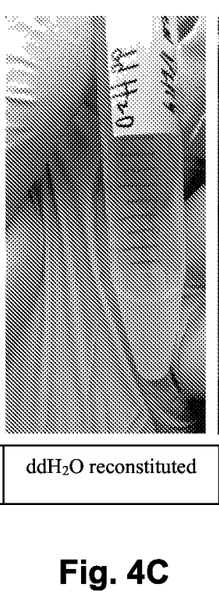
FIG. 4C shows non-sterilized lyophilized pre-gel reconstituted in deionized water.
Figure 4D:
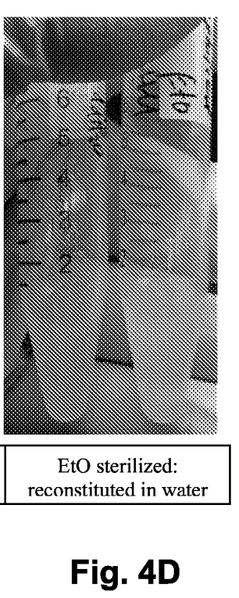
FIG. 4D shows lyophilized pre-gel sterilized with EtO and reconstituted either in water or HCl. Comparison of FIGS. 4B-4C shows that reconstitution was complete for all samples except those after sterilization in HCl (FIG. 4D).

Due to the ineffective hydrogel formation after terminal sterilization of the pre-digest decellularized ECM material, and recognizing the clinical/commercial need for sterilization, we hypothesized that changing the form of material prior to sterilization would allow for ECM gelation. Instead of the lyophilized solid ECM sheets, we sterilized a lyophilized pre-gel prepared from non-dialyzed (intact ECM as described above), mechanically comminuted ECM that is enzymatically digested essentially as described above) and tested whether hydrogel formation would occur. ECM derived from small intestinal submucosa (SIS-ECM) was decellularized according to a standard protocol without dialysis. The SIS-ECM powder was enzymatically digested in the same manner as above, frozen at −80C on dry ice, and lyophilized. The lyophilized pre-gel was then sterilized by exposure to EtO gas at a dose of 750 mg/h for 16 h and/or reconstituted in deionized water or 0.01N HCl (FIGS. 6A-6D). FIGS. 6A-6D show complete reconstitution at room temperature using water and HCl prior to sterilization but after sterilization (FIG. 4D) only pre-gel in deioinized water was completely reconstituted.

Figure 5:
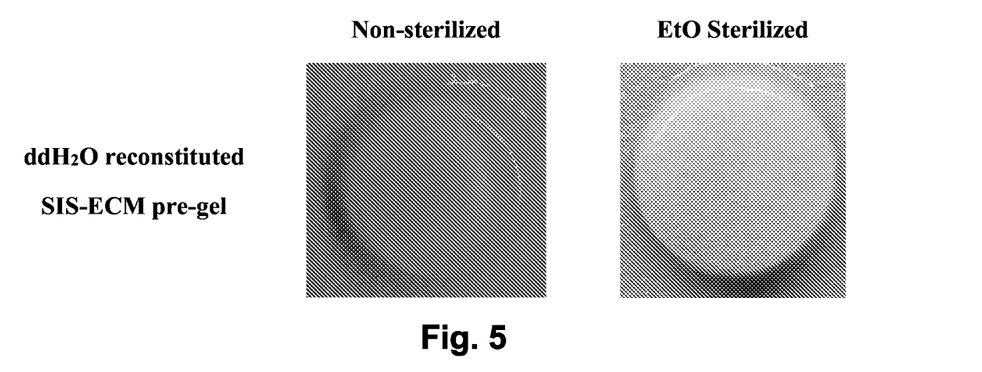
FIG. 5 shows sterilization of lyophilized SIS-ECM pre-gel results in hydrogel formation.

Since only pre-gel in deionized water was completely reconstituted, these samples were tested for hydrogel formation. FIG. 5 shows that both non-sterilized and EtO sterilized pre-gel resulted in a solid gel when neutralized and placed in a 37° C. incubator without $CO_2$, which maintained form after removal of metallic ring molds.

Figure 6:
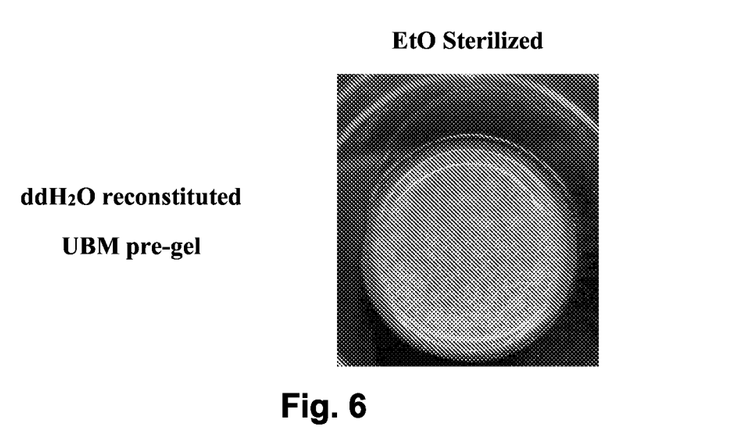
FIG. 6 shows sterilization of lyophilized UBM pre-gel results in hydrogel formation.

To corroborate the results shown in FIG. 5, ECM derived from urinary bladder (UBM) was decellularized according to a standard protocol and tested in the same manner as the SIS-ECM, above. The results similarly showed that sterilization of the lyophilized pre-gel was conducive to hydrogel formation (FIG. 6).

Example 11—Sterilization of Lyophilized Product—Further Studies

Expanding the work of the Examples above, ECM materials, prepared essentially as described above, are sterilized in different forms, as follows: ECM material that is not digested, both in powder and 2D sheet form; hydrated powder or 2D sheet ECM material that is not digested; pre-gel solution that is acid-protease digested, but not neutralized; and/or lyophilized pre-gel that is digested, but not neutralized. ECM material from various sources are tested, including urinary bladder, spleen, liver, heart, pancreas, ovary, small intestine, central nervous system (CNS), adipose tissue, and/or bone.

The materials are sterilized by ethylene oxide, gamma radiation (2 kGy, 30 kGy @ ambient and −80° C.), electron beam radiation (2 kGy, 30 kGy @ ambient and −80C), and/or supercritical $CO_2$ (low and/or high). A non-sterilized control also is run.

Figure 7A:
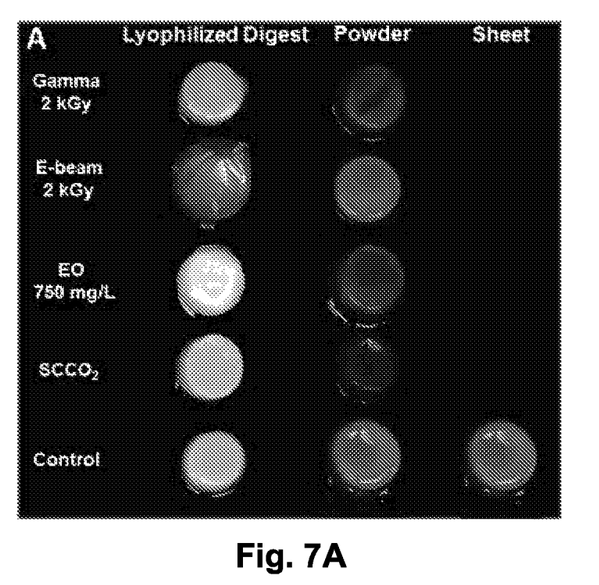
FIG. 7A is a comparison of various sterilization methods of decellularized UBM.
Figure 7B:
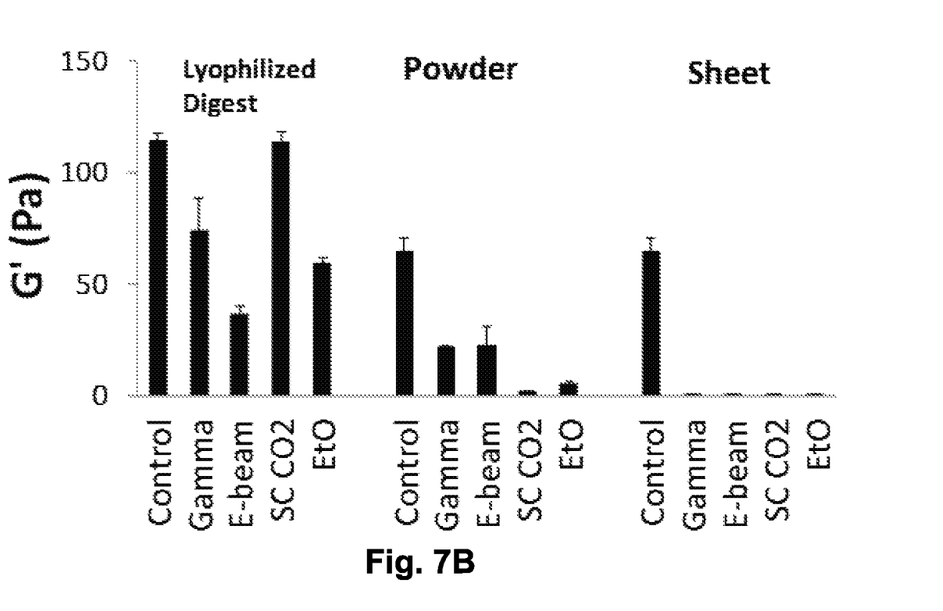
FIG. 7B is a qualitative comparison of FIG. 7A.

Example 12—Decellularized Urinary Bladder Matrix (UBM) Subjected to Various Sterilization Methods Urinary bladder matrix was decellularized according to a standard protocol and subjected to various sterilization methods. Hydrogel formation was tested following sterilization of (1) the UBM sheet, (2) mechanically comminuted UBM powder, and (3) following digestion and lyophilization. Each gel was formed in a ring mold and imaged (FIG. 7A). Hydrogel formation was then tested with the most rigid hydrogels formed by the lyophilized digests, followed by the powder form, as shown by the storage modulus values (see FIG. 7B). Sterilization of the UBM sheet did not allow for subsequent hydrogel formation. Each sterilization method has an impact upon hydrogel formation but this can be mitigated by the starting form of the ECM material, most clearly evidenced by a comparison of the storage moduli of the $scCO_2$ and EtO lyophilized digest versus powder forms. Interestingly, the non-sterilized control samples also show a distinct difference in hydrogel formation with the lyophilized digest forming a more rigid gel. Qualitatively, the lyophilized digest formed the most rigid hydrogel followed by powder while sterilization of the UBM sheet did not allow for subsequent hydrogel formation. The qualitative trends in gel rigidity were corroborated by rheological characterization of the gel stiffness (i.e., storage modulus or G'). Together, these Figures highlight the importance of the form of ECM (i.e., sheet, powder, or digest) that is exposed to sterilization.

Example 13—Preparation of Non-Gelling Solubilized ECM

1—Decellularize a tissue of interest (e.g., small intestine, urinary bladder, liver, bone, etc.)

2—Sterilize the ECM with a method of terminal sterilization (e.g., exposure to ethylene oxide or ionizing radiation). Sterilization can be performed on ECM in dry or hydrated forms and in sheet or powder forms.

3—After sterilization, mechanically comminute and solubilize the ECM by enzymatic digestion (e.g., with pepsin).

4—Neutralize the salt concentration and pH of the solubilized ECM and the soluble, non-gelling ECM is ready for use.

Example 14—Use of Non-Gelling Solubilized ECM for Treatment of Rheumatoid Arthritis The technology could be used to treat individuals with rheumatoid arthritis, for example, or other inflammatory joint conditions. Whereas current treatment is intraarticular injection of a corticosteroid, which is associated with poor side-effects, a soluble extracellular matrix (ECM) prepared as described herein, would act to reduce local inflammation. Particularly in the intraarticular space it is important that the ECM be soluble but non-gelling so there is not a physical obstruction to articular movement.

Example 15—Evaluation of Non-Gelling Solubilized ECM

Figure 8:
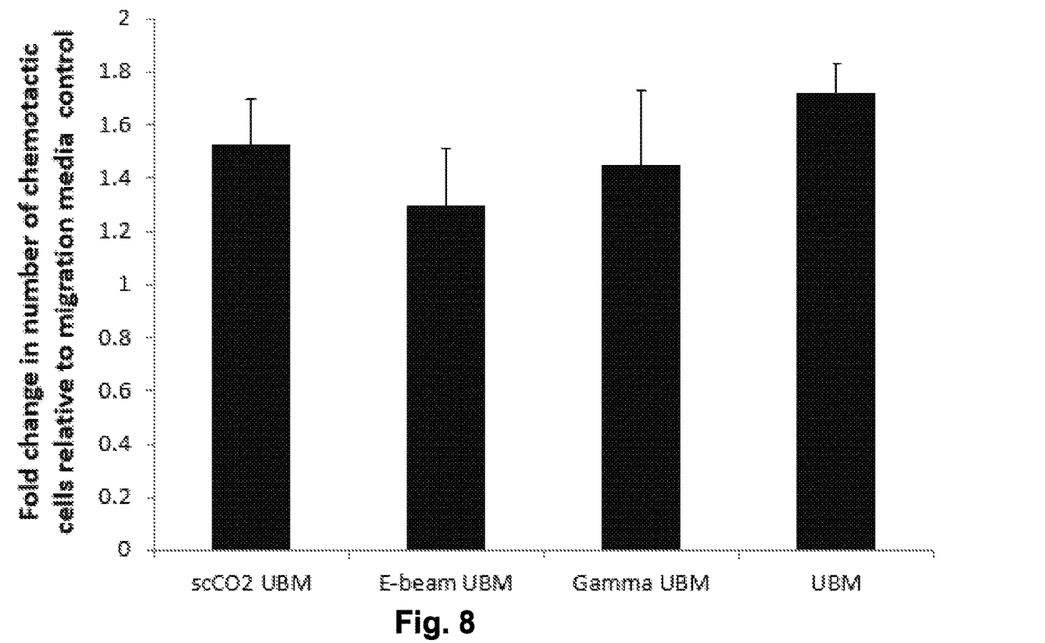
FIG. 8 is a graph showing chemotactic response of perivascular stem cells (PVSCs) to non-sterilized urinary bladder matrix (UBM) and sterilized (scCO$_2$, E-beam or gamma) UBM.

Urinary Bladder Matrix was prepared by accepted protocol: mechanical delamination, washed in 0.1% peracetic acid, and rinsed in saline and water, essentially as described herein. The material was then lyophilized and separated into groups based on sterilization treatment of 30 kGy gamma irradiation, 30 kGy electron beam irradiation, and supercritical $CO_2$ sterilization. Following sterilization, each scaffold was ground to particulate and solubilized in a pepsin buffer for 24 hours. The pH and salt concentration in the digest was then balanced essentially as described herein for preparation of an ECM hydrogel, and lack of gelation was validated by warming to 37° C. prior to use in experiments. Sterilization in this manner prevented gelation independent of choice of sterilization method FIG. 8 shows chemotactic response of perivascular stem cells (PVSCs) to non-sterilized urinary bladder matrix (UBM) and sterilized ($scCO_2$, E-beam or gamma) UBM. Chemotaxis assays were performed in standard chambers with 8 µm filters (Neuro Probe, Gaithersburg, Md.) coated with rat-tail collagen (BD Biosciences, San Jose, Calif.). Solubilized sterilized and non-sterilized UBM samples were loaded into the bottom wells of the chamber and the collagen coated filter was placed on top. PVSCs were grown to 90% confluence before overnight incubation in DMEM with 0.5% heat inactivated FBS. Cells were trypsinized and resuspended in DMEM and 30,000 cells were loaded into the top well of the chemotaxis chamber, separated from the bottom by the filter. Chambers were placed into a humidified atmosphere at 37° C. with 5% $CO_2$ for three hours. Migrated cells were stained with DAPI (Fisher Scientific, Waltham, Mass.), imaged using a Zeiss Axio-Observer Z.1 microscope (Oberkochen, Germany) with 10× objective and quantified with ImageJ (NIH, Bethesda, Md.). Changes in chemotactic response for non-sterilized and sterilized UBM were expressed as a fold change compared to migration media control. There was no significant difference in the chemotactic response of PVSCs to UBM or sterilized UBM.

Figure 9:
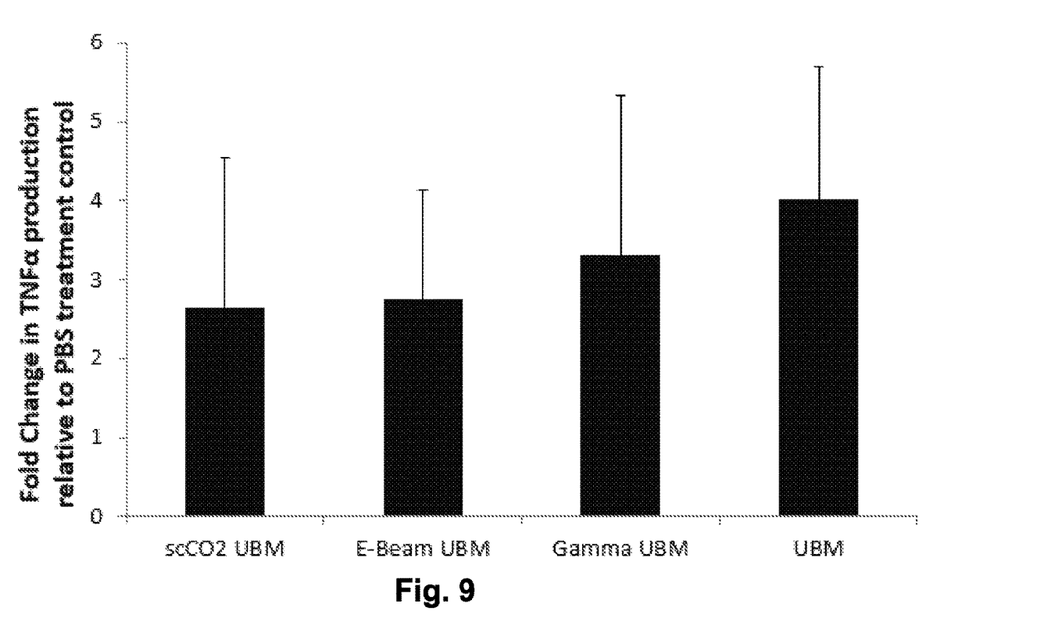
FIG. 9 is a graph showing TNFα production of human monocyte derived macrophages in response to treatment with UBM or sterilized (scCO$_2$, E-beam or gamma) UBM.

FIG. 9 shows TNFα production of human monocyte derived macrophages in response to treatment with UBM or sterilized ($scCO_2$, E-beam or gamma) UBM. Human monocytes (THP-1 ATCC TIB-202) were exposed to 320 nM phorbol 12-myristate (PMA) for 24 hours to induce differentiation into macrophages. Adherent macrophages were washed in PBS and placed in fresh media for 48 hours and then treated with solubilized non-sterilized or sterilized UBM for 48 hours. Culture supernatants were centrifuged to pellet the cells and debris; supernatants were harvested and frozen at −80° C. Quantification of TNFα production was undertaken using a commercially available ELISA kit (BD Bioscience, San Jose, Calif.) and TNFα production was normalized to PBS treatment control. There was no significant difference in TFNα production when macrophages were exposed to UBM or sterilized UBM.

The present invention has been described in accordance with several examples, which are intended to be illustrative, rather than limiting, in all aspects. Thus, the present invention is capable of many variations in detailed implementation, which may be derived from the description contained herein by a person of ordinary skill in the art, and should not be limited by the preceding description, but should be construed to be as broad in scope as the following claims.

We claim:

1. A method of preparing a non-gelling, solubilized extracellular matrix composition, comprising: (i) sterilizing intact extracellular matrix (ECM) material, (ii) solubilizing the sterilized intact ECM material by digestion with an acid protease in an acidic solution to produce a digest solution, and (iii) raising the pH of the digest solution to a pH between 7.2 and 7.8 to produce a non-gelling, solubilized ECM composition that does not form a gel at 37° C.

2. The method of claim 1, wherein the ECM material is not dialyzed or subjected to a cross-linking process prior to the solubilizing step.

3. The method of claim 1, in which the ECM material is sterilized using gamma radiation, electron beam radiation, ethylene oxide, and/or supercritical $CO_2$.

4. The method of claim 1, wherein the ECM material is prepared from mammalian tissue.

5. The method of claim 4, wherein the ECM material is prepared from one of urinary bladder, spleen, liver, heart, central nervous system, adipose tissue, bone, pancreas, ovary, or intestine.

6. The method of claim 4, wherein the mammalian tissue is intestine tissue.

7. The method of claim 1, wherein the acid protease is pepsin.

8. The method of claim 7, wherein the ECM material is solubilized at a pH between 3 and 4.

9. The method of claim 1, wherein a base or isotonic solution is added to raise the pH of the digest solution.

10. The method of claim 1, further comprising administering the non-gelling, solubilized ECM composition to a patient.

11. The method of claim 10, wherein the patient is a human patient.

12. The method of claim 1, further comprising integrating one or more of a cell, a drug, a cytokine and a growth factor into the non-gelling, solubilized ECM composition.

13. The method of claim 1, further comprising coating a matrix of a biocompatible scaffold with the non-gelling, solubilized ECM composition.

14. A solubilized, non-gelling ECM composition prepared by a process according to claim 1.

15. The method of claim 13, in which the scaffold comprises an inorganic mineral comprising calcium, a ceramic material, and/or a polymer.

16. A biocompatible device comprising a hybrid extracellular matrix scaffold prepared according to the method of claim 13.

17. The device of claim 16, in which the device is a prosthesis.

18. A method of attaching a device to tissue and/or structures of a patient, the device comprising a hybrid extracellular matrix scaffold prepared according to the method of claim 13, the method comprising growing or embedding a patient's cells into the hybrid extracellular matrix scaffold for a time period sufficient for in-growth of the patient's cells into the scaffold.

19. The method of claim 18, in which the hybrid extracellular matrix scaffold is contacted with the cells and the in-growth occurs in vivo.

20. The method of claim 18, in which the hybrid extracellular matrix scaffold is contacted with the cells and the in-growth occurs ex vivo.

\* \* \* \* \*